United States Patent [19]

Champaigne

[11] Patent Number: 4,523,146
[45] Date of Patent: Jun. 11, 1985

[54] MASS FLOW INDICATOR FOR METAL PARTICLES

[76] Inventor: Jack M. Champaigne, 502 E. LaSalle Ave., South Bend, Ind. 46617

[21] Appl. No.: 582,298

[22] Filed: Feb. 22, 1984

Related U.S. Application Data

[62] Division of Ser. No. 390,254, Jun. 21, 1982, abandoned.

[51] Int. Cl.³ ............................................. G01N 27/74
[52] U.S. Cl. ..................................... 324/204; 324/236
[58] Field of Search ......... 73/432 DS, 861.04, 861.08, 73/861.11; 324/204, 234, 236, 237, 239

[56] References Cited

U.S. PATENT DOCUMENTS 2,760,769 8/1956 Onstad ................................ 324/204
3,970,036 7/1976 Baer et al. ........................... 324/236
4,195,260 3/1980 Sakamoto et al. .................. 324/204

OTHER PUBLICATIONS

Ogren, "Sensor Circuit Utilizing Variable Inductance Input", in I.B.M. Tech. Disclosure Bulletin, vol. 14, #4, 9/71.

Primary Examiner—Herbert Goldstein
Attorney, Agent, or Firm—James D. Hall

[57] ABSTRACT

A method for determining the size of metal particles which includes the positioning of an inductive circuit within a particle flow path to establish an oscillatory signal, varying the signal frequency to determine at which amplitude a signal is substantially constant, and then recording changes in signal amplitude which correlate to changes in particle size.

2 Claims, 3 Drawing Figures

MASS FLOW INDICATOR FOR METAL PARTICLES

This application is a division of application Ser. No. 390,254, filed 6-21-82, now abandoned.

BACKGROUND OF THE INVENTION

This invention relates to a device for determining the flow rate of metallic paramagnetic and ferromagnetic particles.

Heretofore devices for measuring the flow rate of a mass of metal particles, such as shot, made use of two selectively spaced inductive coils. The coils were magnetically coupled with one coil acting as the primary with some convenient time-varying current excitation and the second coil acting as a secondary with a volt meter as a load. As the flow of particles through the coupled coils increases, the mutual magnetic coupling increases with such increase being displayed on the volt meter. The volt meter reading is then scaled to indicate the rate of mass flow of the particles.

In the above described prior art two-coil method of flow rate measurement both coils must be mounted concentrically and spaced a selected distance for accurate measurements. Additionally, at low particle flow rates, the mass of the particles passing through the coils is generally not enough to create a sufficient mutual magnetic coupling between the coils. Therefore, at low particle flow rates an erroneous reading is obtained by using the two-coil arrangement.

The following describes an improved mass flow rate detector which utilizes only a single coil and which is extremely accurate in measuring low, as well as high flow rates of metal particles.

SUMMARY OF THE INVENTION

In this improved invention, a single inductive coil is placed within the flow path of the metallic paramagnetic and ferromagnetic particles so that the particles pass through the center of the coil. The coil forms a part of an LC circuit. As the particle flow rate through the coil increases or decreases, the permeability within the coil changes so as to vary the inductance of the LC circuit and, thereby, vary the frequency and amplitude of the signal produced by the LC circuit. This change in frequency or amplitude of the output signal from the LC circuit is converted into a suitable readout which is preferably scaled into convenient flow rate terms, such as pounds per minute.

A related aspect of this invention utilizes the coil of an inductive tuned circuit to determine the size of the metal particles passing through the coil. This is determined by varying the frequency of the oscillatory signal produced by the circuit during periods of flow of the metal particles through the coil and during periods of no particle flow through the coil. It has been found that for each particle size a particular frequency exists, such that variations in particle flow rate have no affect on the amplitude of the oscillatory signal. If this particular frequency of oscillation is established in the coil, introduction of flow of a specific particle size will affect the frequency only, but not the amplitude. Therefore, if a specific size of particle is flowing and the amplitude is noted, any change of amplitude may be correlated to different sizes of particles for both larger particles and smaller particles or mixtures of such particles.

Accordingly, it is an object of this invention to provide an efficient and accurate mass flow indicator for metal particles.

Another object of this invention is to provide a device for determining the mass flow rate of metal particles utilizing a single inductive coil of an LC circuit.

Still another object of this invention is to provide a device for determining the flow rate of metal particles, such as shot, and which is accurate at low as well as high rates of flow of the particles.

Another object of this invention is to provide a method of determining size of metal particles as such particles pass along a flow path.

Other objects of this invention will become apparent upon a reading of the following description.

DESCRIPTION OF THE PREFERRED EMBODIMENT

The preferred embodiment illustrated is not intended to be exhaustive or to limit the invention to the precise form disclosed. It is chosen and described in order to best explain the principles of the invention and its application and practical use to enable others skilled in the art to best utilize the invention.

Figure 1:
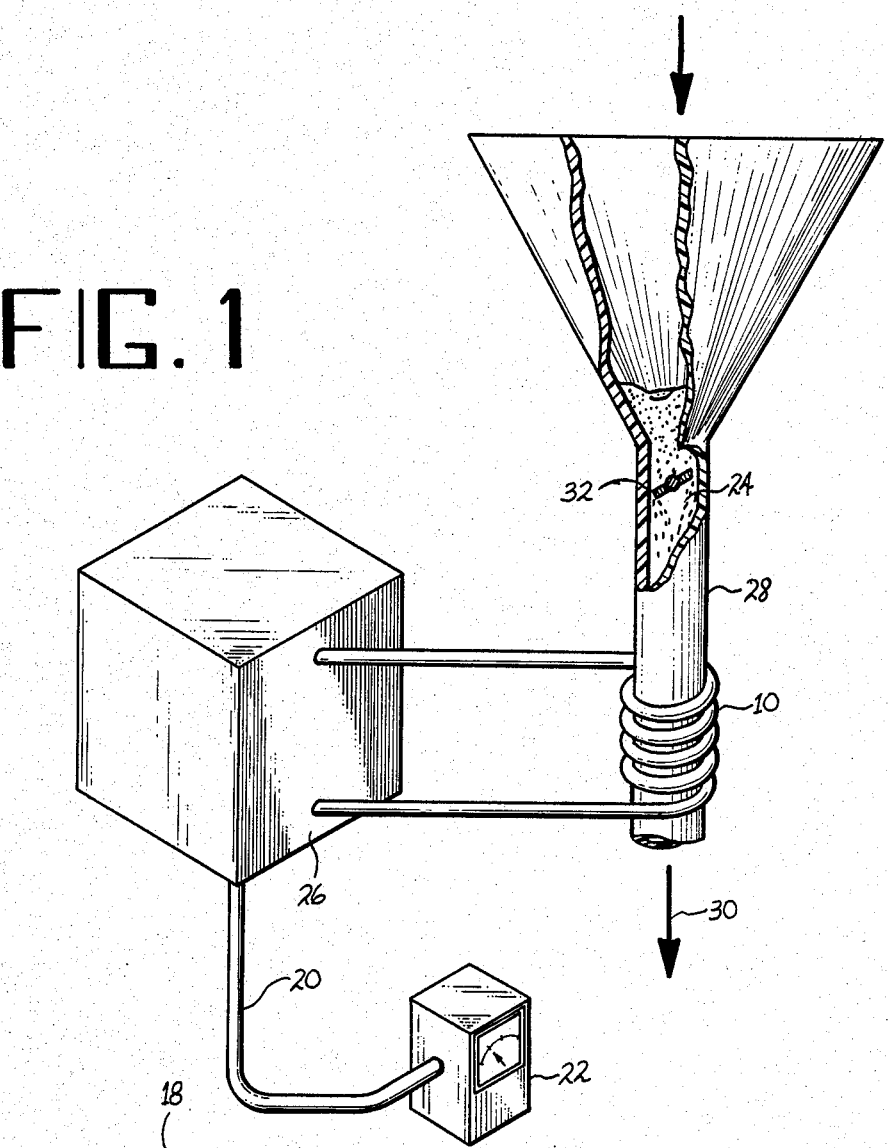
FIG. 1 is a perspective view of one embodiment of the flow rate indicator of this invention with portions of the funnel device forming the flow path for the particles being broken away for purposes of illustration.
Figure 2:
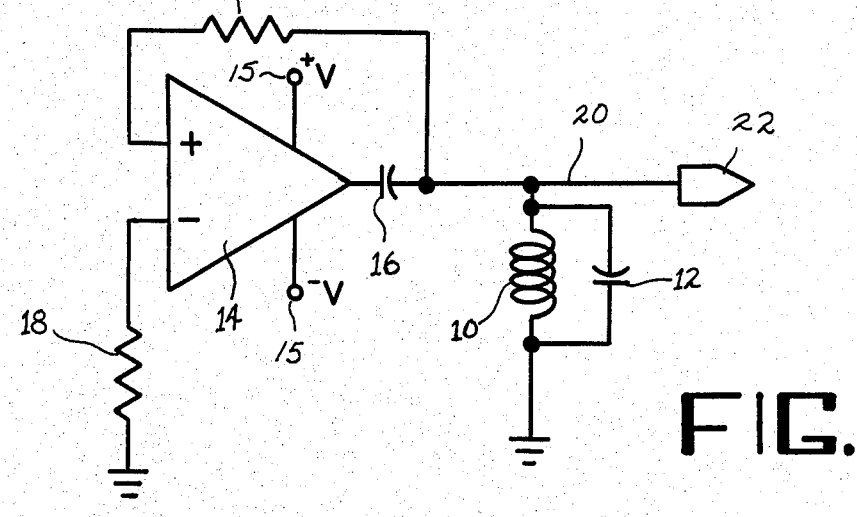
FIG. 2 is a circuit diagram of the LC and amplifier circuit for the flow device of FIG. 1.

The mass flow indicator shown in FIGS. 1 and 2 includes a coil 10 to which is connected a capacitor 12 in parallel to form a basic LC circuit. An IC operational amplifier 14 is connected through a coupling capacitor 16 to coil 10 and capacitor 12 of the LC circuit. The capacitance of the LC circuit could be obtained by other than a separate capacitor, such as through the parasitic capacitance of the coil windings for example. Amplifier 14 and coupling capacitor 16 are used to maintain oscillation of the LC circuit at its resonant frequency. Resistors 18 in the feedback line of amplifier 14 and to ground provide input protection to the amplifier. The oscillatory output signal of the circuit of FIG. 2 passes by line 20 into a frequency indicator 22 which provides a display of the frequency or the amplitude of the frequency scaled in convenient terms for purposes of correlation to the flow rate of the metal particles 24 while passing through coil 10. Frequency indicator 22 can be a common analog circuit frequency meter which converts frequency to a voltage correlated to a meter readout. With the exception of coil 10, the components of the circuit of FIG. 2 are located within diagramic housing 26. A power source, such as a 110-volt AC line current, is provided for the circuit of FIG. 2. The AC power input is DC rectified by suitable bridge or rectification circuit with the voltage being stepped down by suitable transformer to the DC input load required across terminals 15 for operational amplifier 14 and the LC circuit.

A tube 28 serves to direct particles 24 along a selected flow path indicated by arrow 30 in FIG. 1. A valve 32 located within tube 28 is utilized to regulate the flow rate of particles 24 through the tube. Coil 10 circumscribes or is wrapped about tube 28 so that particles 24 pass through the inside of the coil. The movement of particles 24 through tube 28 may be by gravity as shown in FIG. 1 or by a mechanical means, such as centrifugal force as is used in some shot peening processes. As particles 24 flow through tube 28 and coil 10, the permeability of the coil changes with the resulting change in coil inductance. The greater the particle mass passing through coil 10, the greater the coil inductance and the lower the frequency of the LC circuit as determined by the formula:

$$f = \frac{1}{2\pi \sqrt{LC}}$$

Such changes in oscillating frequency of the circuit FIG. 2 is reflected as a readout on frequency indicator 22. Such a readout is correlated to the mass flow rate of particles 24. Additionally, it has been found that the signal produced by the LC circuit produces a change not only in frequency of the signal but also in its amplitude. Increasing the mass flow of small size particles 24 will display an increase in the signal amplitude of the oscillator circuit. Increasing the mass flow of large size particles 24 will produce a decrease in the amplitude of the oscillating signal. Therefore, by selected pretesting, the flow rate of specific small and large size particles 24 can be monitored by observing the amplitude changes of the oscillating signal produced by the LC circuit. Such an observed change in signal amplitude can be utilized in addition to changes in frequency of the oscillating signal to determine mass flow rate of particles 24.

Figure 3:
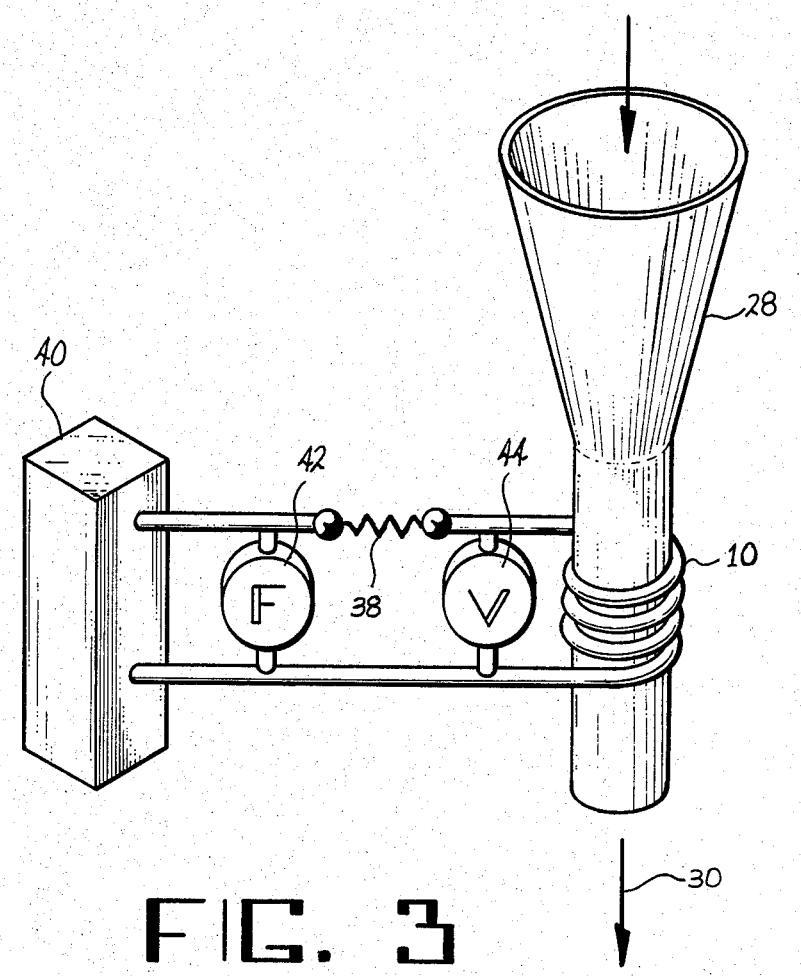
FIG. 3 is a perspective schematic view of a modified embodiment of this invention by which the size of the metal particles can be determined.

The schematic embodiment of the invention shown in FIG. 3 relates to a device by which the size of metallic particles 24 can be determined while flowing through tube 28 along flow path 30. An inductive tuned circuit such as the RL circuit shown is utilized with coil 10 being wrapped around or circumscribing tube 28. Completing the RL circuit is resistor 38 used in series with a sweep generator 40. Sweep generator 40 varies the frequency of the RL circuit. Connected across coil 10 are a frequency meter 42 and an AC volt meter 44. Volt meter 44 serves as an amplitude detector for the oscillating signal of the circuit and frequency indicator 42 may be of the voltage converter type in integrated circuit form or a conventional digital counter type.

It has been found that for a specific metal particle size, the amplitude of the oscillatory signal generated by sweep generator 40 will be substantially constant for a particular frequency at both flow and non-flow conditions of the particles through tube 28. This particular frequency for a specific size particle can be determined by observing a constant reading at volt meter 44 during periods of flow of the particles through tube 28 and stopped or no-flow of the particles and noting the frequency of the signal at meter 42 when this constant volt meter reading occurs. For each of several reference size particles, the critical of particular frequency at which there is no signal amplitude charge during flow and no-flow conditions is determined.

If it is desirable to operate a process using a particular size of particle, then the critical frequency for that size particle is established and its constant amplitude of oscillation is noted. The introduction of different size particles in tube 28 will cause a variation in the signal amplitude and this variation will be displayed on a meter 44 and this meter may be calibrated to show the amount of variation in particle size. Usually in a shot peening process this indicates a breaking down of particles from the original round, spherical size used in peening to the broken, shattered pieces which are undesirable.

In addition to the above procedure, another method may be employed whereby the particles are introduced into the flow path periodically and the amplitude variation monitored at meter 44. The frequency of oscillation would be varied by sweep generator 40 until no amplitude variation occurred. At this critical frequency a size determination can be made by referring to a predetermined chart. Each particle size has its own unique, critical frequency.

It is to be understood that the invention is not to be limited to the details above given but may be modified within the scope of the appended claims.

What I claim is:

1. A method of determining the size of metal particles as such particles pass along a flow path comprising the steps:
    (a) Establishing an oscillatory signal in a coil of an inductive tuned circuit placed within said flow path;
    (b) Varying the frequency of said signal during periods of flow and no flow for a specific size of said particles along said flow path and determining that particular frequency at which the amplitude of said signal is substantially constant; and
    (c) Driving said coil at said particular frequency while passing said particles along said flow path through the coil and observing any changes in signal amplitude, said changes in signal amplitude being correlated to changes in particle size.

2. A method of determining the size of metal particles as such particles pass along a flow path comprising the steps:
    (a) Establishing an oscillatory signal in a coil of an inductive tuned circuit placed within said flow path;
    (b) Varying the frequency of said signal during periods of flow and no flow for a specific size of said particles along said flow path and determining that particular frequency at which the amplitude of said signal is substantially constant; and
    (c) Driving said coil at variable frequencies while passing said particles along said flow path through the coil and observing the particular frequency at which no change in signal amplitude takes place between flow and no flow, said particular frequency being correlated to particular particle size.

* * * * *